(12) United States Patent
Israël et al.

(10) Patent No.: US 7,279,330 B1
(45) Date of Patent: Oct. 9, 2007

(54) METHOD FOR IDENTIFYING MODULATING COMPOUNDS OF NEUROTRANSMITTERS

(75) Inventors: Maurice Israël, Bures-sur-Yvette (FR); Bernard Lesbats, Plessis-Pate (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 82 days.

(21) Appl. No.: 10/049,296

(22) PCT Filed: Aug. 10, 2000

(86) PCT No.: PCT/FR00/02294

§ 371 (c)(1),
(2), (4) Date: Aug. 6, 2002

(87) PCT Pub. No.: WO01/13108

PCT Pub. Date: Feb. 22, 2001

(30) Foreign Application Priority Data

Aug. 11, 1999 (FR) .................................. 99 10410

(51) Int. Cl.
*C12N 5/08* (2006.01)
*C12N 5/06* (2006.01)

(52) U.S. Cl. ...................... 435/368; 435/325; 435/347; 435/352; 435/353; 435/354; 435/363; 435/366; 435/374; 435/378; 435/379

(58) Field of Classification Search ................ 435/325, 435/352, 353, 354, 363, 366, 368, 378, 379
See application file for complete search history.

(56) References Cited

FOREIGN PATENT DOCUMENTS

WO      WO92/19717      11/1992

OTHER PUBLICATIONS

Reddy & Sastry (May 25, 1979) "Studies on neurotransmitter-stimulated phospholipid metabolism with cerebral tissue suspensions: a possible biochemical correlate of synaptogenesis in normal and undernourished rats." Brain Research 168(2): 287-298.*
Garthwaite et al. (1980) "A Morphological Study of Incubated Slices of Rat Cerebellum in Relation to Postnatal Age." Dev. Neurosci. 3(2): 90-99.*
Weights and Measures Table retrieved from Google on Mar. 12, 2004.*
M. Israel et al., *Journal of Neurochemistry*, (Dec. 1996), 67(6), pp. 2624-2627.
M. Israel et al., *Neurochemistry International*, (Jan. 1993), 22(1), pp. 53-58.
Y.M. Gaudry-Talarmain et al., *European Journal of Pharmacology*, (Aug. 1989), 166(3), pp. 427-433.
M. Israel et al., *Journal of Neurochemistry*, (Jul. 1982), 39(1), pp. 248-250.
J. Bockaert et al., *Journal de Physiologie*, (1986), vol. 81, pp. 219-227.
A. Helme-Guizon et al., *European Journal of Neuroscience*, (Jul. 1998), 10(7), pp. 2231-2237.
P. Schaeffer et al., *Brain Research*, (1991), vol. 539, pp. 155-158.

* cited by examiner

*Primary Examiner*—Janet L. Andres
*Assistant Examiner*—Gregory S. Emch
(74) *Attorney, Agent, or Firm*—Buchanan, Ingersoll & Rooney, PC

(57) ABSTRACT

A process for identifying compounds that can modulate the release of neuromediators is described in which, for example, at least one compound that is to be tested is brought into contact with a nerve tissue preparation and the possible modulating effect of the compound on release of neuromediator by the nerve tissue preparation is determined. Methods of preparing calibrated pieces of mammalian cerebral material and kits for the implementation of the process are also described.

11 Claims, 11 Drawing Sheets

FIG. 3A
Acetylcholine
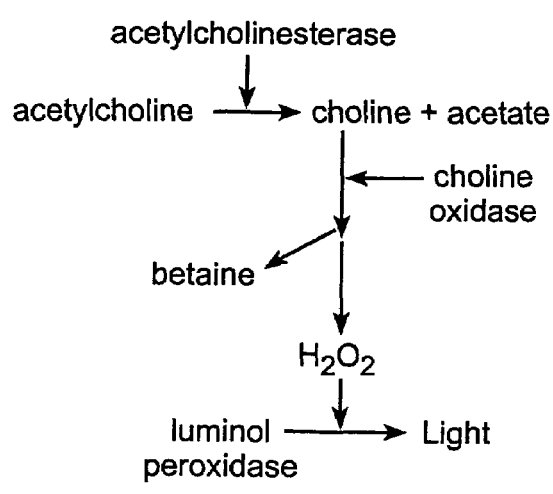
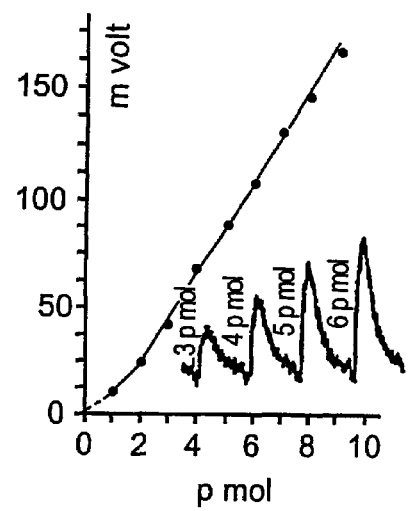

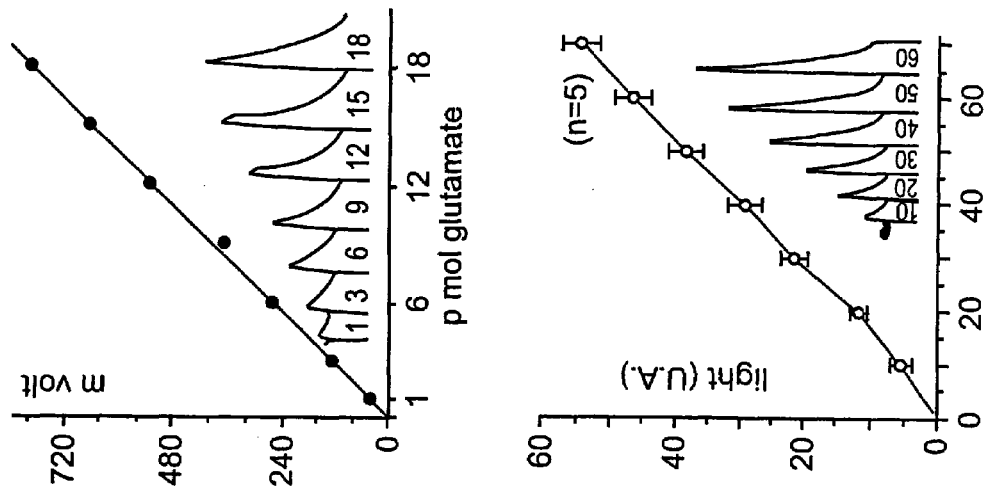
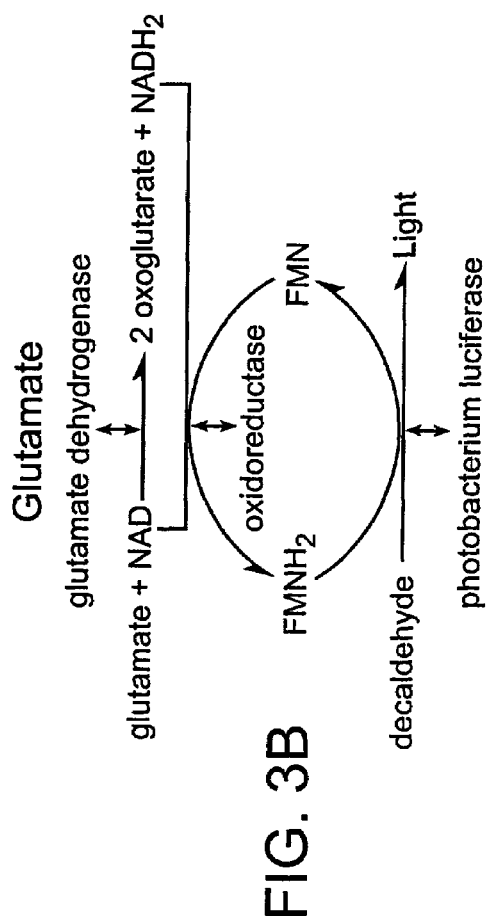
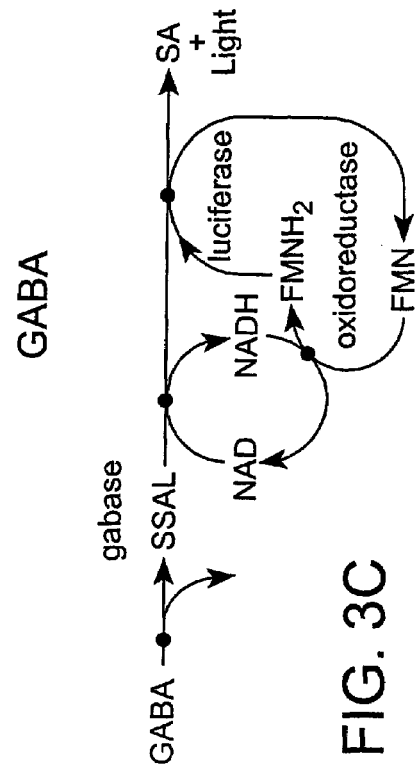
FIG. 3B
FIG. 3C

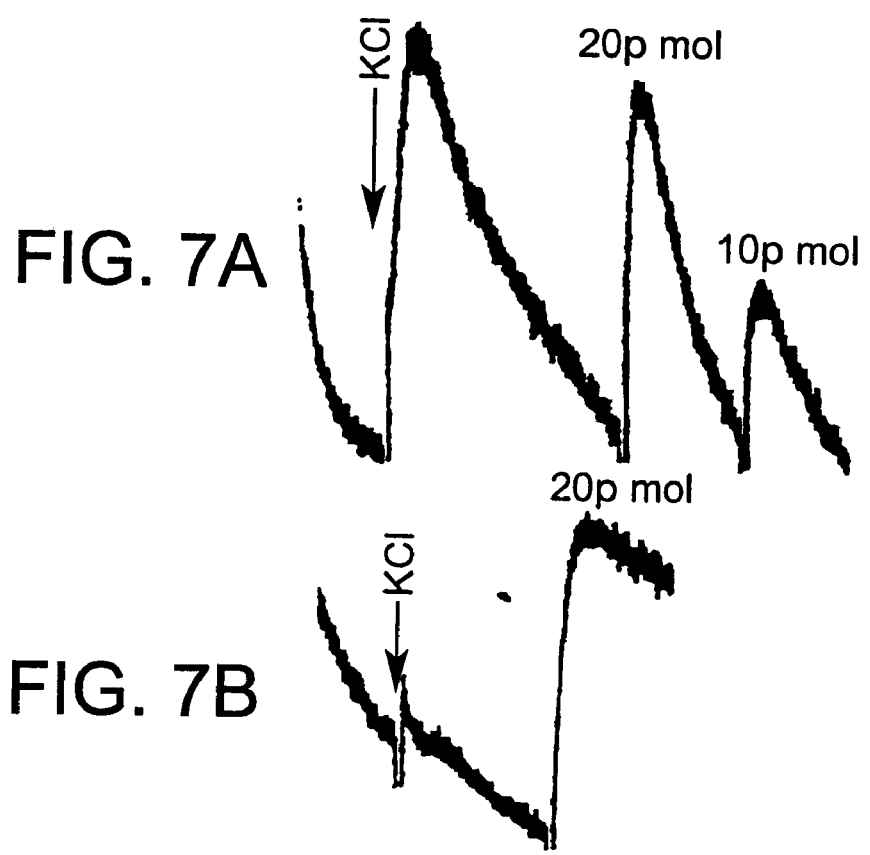

FIG. 10
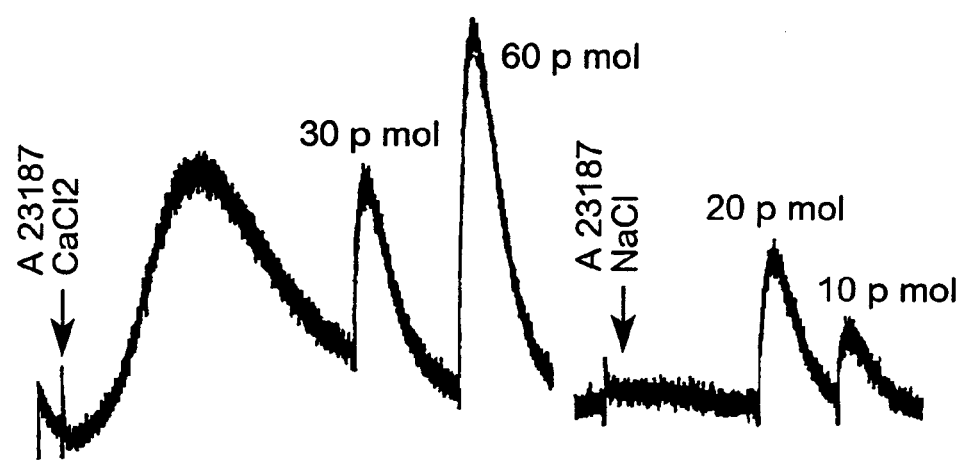

METHOD FOR IDENTIFYING MODULATING COMPOUNDS OF NEUROTRANSMITTERS

This invention relates to compositions and methods for the demonstration or the characterization of compounds that actuate the release of neuromediators. It also relates to the nerve tissue preparation that is useful for implementing these methods, and the use of the compounds that are thus identified or characterized as therapeutic agents or as leads for the development of therapeutic agents.

Aware of the problems that attacks on the nervous system pose in our society, whether they be neurodegenerative or linked to mental tone (depression, psychosis) or to traumas, the pharmaceutical groups and the academic research entities have launched ambitious projects whose purpose is to understand and to prevent these pathologies. For this purpose, new therapies, based on the graft of modified cells that secrete medication, as well as the discovery of new products that ensure prevention or pretreatment have become priority objectives for many laboratories. It is necessary, however, to understand that the central neurotransmissions as well as the processes that regulate them are complex and that it is often difficult to locate the target of endogenic or exogenic neurotoxicants. It is therefore essential to use technologies that make it possible to explore quickly a large number of products that act on a considerable series of potential targets.

The methods that are used today by the pharmaceutical industry are long, cumbersome and labor-intensive. These methods thus are based primarily on the study of what happens after the release of the neuromediators, e.g., the study of post-synaptic events.

This invention proposes new methods and compositions that make it possible to deal with the study, the prevention and the treatment of the pathologies of the nervous system with greater chances of success. This invention is based in particular on the study of the modulation of neurotransmission by its pre-synaptic aspect. The invention therefore makes it possible to act not on the effects or on the symptoms, but directly on the origin and the causes of pathologies. This invention makes possible the simultaneous study of many test compounds on preparations of nerve tissue and offers significant levels of reliability and reproducibility.

This object is achieved according to this invention, thanks to a process for identifying compounds that can modulate the release of neuromediator, characterized in that at least one compound that is to be tested is brought into contact with a nerve tissue preparation and in that the possible modulating effect of said compound on the release of neuromediator by said nerve tissue preparation is determined.

This invention is remarkable in that it offers a series of meterings of neurotransmitters that are quick, simple, sensitive and reliable and that can be used in real time in living preparations, such as perfused brains, tissue sections, isolated nerve endings (synaptosomes), cell cultures, etc. The focus of the process according to the invention is the release of neuromediators, i.e., on the pre-synaptic plane of the neurotransmission, whereas the investigation techniques that are described in the prior art relate to post-releasing aspects, such as the action on the receptors, the recapture inhibitors or degradation enzyme inhibitors of the neuromediators.

According to a preferred embodiment, the process of the invention is characterized in that at least one compound that is to be tested is brought into contact with a nerve tissue preparation, then said preparation or its supernatant is brought into the presence of one or more substances of which at least one is able to react with a neuromediator that is released by the nerve tissue preparation and in that the possible modulating effect of the compound or compounds to be tested is determined by detecting or by metering one or more of said detectable substances if a neuromediator is released, or by detecting or by metering at least one product that results from the transformation of one of said substances if a neuromediator is released.

Bringing into contact the nerve tissue preparation with the compound or compounds to be tested is carried out during an adequate period to allow said compound to express a possible effect on said preparation.

The process of the invention makes it possible to test isolated compounds, a mixture of compounds, a biological sample, a combinatorial bank, a synthetic or natural molecule, etc. It may involve a known product, of which it is desired to characterize the activity, or unknown products or undefined mixtures. As indicated below, the invention describes nerve tissue preparations that make it possible to use a large number of samples of cerebral material from a single animal, which makes it possible to test simultaneously or sequentially large amounts of compounds, in particular compound banks.

The process of the invention thus can consist in bringing several compounds to be tested into contact either sequentially or simultaneously, in parallel or not, with the nerve tissue preparation.

For a simultaneous bringing into contact, the compound or compounds that are tested are, for example, put into solution with the detectable substance, then the mixture that is obtained is brought into contact with the nerve tissue preparation. In another embodiment, the tested compound or compounds and the solution that comprises the substance or substances of which at least one is able to react with a neuromediator are conditioned separately and introduced simultaneously in the medium that comprises the nerve tissue preparation. The supernatant is then harvested and the metering is carried out.

For a sequential bringing into contact, the nerve tissue preparation can be brought into contact in a first step with the solution that comprises one or more substances of which at least one is able to react with a neuromediator. This optionally makes it possible to eliminate the background noise that is linked to the optional presence of residual neuromediator in the medium. In a second step, the tested compound or compounds are added, and the detectable substance is metered.

In addition to testing several compounds, however, the process of the invention also makes possible the metering of several neuromediators in parallel. Thus, the same compound can be tested in parallel for its properties in the release of various neuromediators, in nerve tissue samples that are prepared from a single animal.

The results that are obtained with the process of the invention and reported in the experimental part below show that this process can be implemented in a manner that is easy, reproducible and fast, on many nerve tissue samples that are biologically significant, to demonstrate new compounds or new properties of known compounds, or to refine the mechanism of action or the specificity of action of known compounds. The compositions and processes of the invention can thus be used for research or development of therapeutic products, or for any other application in the nervous system domain.

This invention also relates to tissue preparations that are useful for the implementation of the process above, obtained ex vivo and able to preserve their essential physiological properties during the entire experiment. These nerve tissue preparations make possible fast meterings of many products that are reproducible and reliable and that actuate the synaptic mechanisms. The invention most particularly relates to preparations of microcubes of cerebral material, which make it possible to test a large number of products from a single animal, whereas the prior techniques require the sacrifice of one animal per molecule and are less significant.

A first type of nerve tissue preparation according to the invention comprises microcubes of mammal cerebral material and preferably cerebral cortex microcubes.

A second type of nerve tissue preparation according to the invention comprises foamy fibers of mammal cerebral material, and preferably foamy fibers of the cerebellum or the hippocampus.

The invention actually relates to the nerve tissue preparation that allows reliable, numerous and reproducible meterings from the same animal. In particular, the focus of the invention is the preparation of microcubes of cerebral material from nerve tissue, in particular from the entire brain, the cortex, the cerebellum or any other nerve tissue. The microcubes have the advantage of preserving the local nerve connections and being adequately oxidized in physiological medium to ensure a viability that is compatible with the methods of the invention.

It is necessary to remember that the fractionation of the central nervous system resulted, in the 1960's, in the purification of nerve endings (synaptosomes). During this time, the interest of neurobiologists in these preparations never waned. While these preparations had been very useful for determining the biochemical composition of synaptic elements or for isolating the proteins that ensure neurotransmission, it is necessary, however, to note that these physiological and pharmacological studies came up against difficulties linked to the brief in vitro service life of these synaptosomes, obtained in the fractionation media that are not adapted to the physiological study. The isolation of the torpedo electric organ synaptosomes in the physiological media then seemed to be an exception since they were able to preserve their physiological properties (membrane potential, synthesis and release of ACh) for at least 48 hours. In any case, mammal nerve tissue preparations that preserve such physiological properties have not been described to date. The microcubes of cerebral material according to the invention therefore have a considerable pharmacological advantage.

The microcubes of cerebral material constitute a preparation that offers multiple advantages. Thus, a microcube sample that is obtained from a cortex is statistically comparable to this entire cortex in the context where the set of neurons that is contained in each microcube is in an environment that is similar to its environment in the whole animal. Each of the neurons keeps a certain number of its connections, and the glial environment remains very stable. These two physiological consistencies are without any doubt responsible for the stability and the long service life of the microcube samples. And even if all the microcubes are not equivalent to one another because of the heterogeneity of the cortex, each population that constitutes the sample is statistically identical.

The microcubes preferably have a mean size of between 0.1 and 5 mm$^3$, preferably between 0.1 and 3 mm$^3$, still more preferably from about 1 mm$^3$. The microcubes can be prepared from nerve tissue by cutting and then passage through one or more grids of defined diameter, for example, between 0.01 and 2 mm. It may involve in particular a nylon fabric, a metallic grid, or any other substrate that is suitable for sieving. An illustration of the microcube preparation is shown in FIG. 1 as an attachment, using the cerebral cortex as the starting nerve tissue.

In a particular embodiment of the process of the invention, after preparation of the microcubes and a consequent number of samples distributed in titration substrates, for example conical tubes or microplate wells, the compound or compounds to be tested are brought into contact with the nerve tissue preparation, then the supernatant on which is performed the metering (in particular by chemiluminescence) of the mediators that are optionally released by the nerve tissue preparation is sampled.

Another advantage of the microcubes resides in their significant stability, even after freezing/thawing. Thus the collecting of these meterings is not limited by the duration of the workday, but the nerve tissue preparations can be preserved for subsequent use. The same preparation therefore makes it possible to determine with certainty the effects of one or more series of compounds on several (in particular five) neurotransmissions in parallel, which makes the comparisons all the easier as the constitution of the cortex of healthy animals is stable.

In addition, these microcubes offer advantages relative to other existing preparations that are used by the pharmaceutical industry:

- Compared to brain sections, the microcube samples are statistically more homogeneous since it is always difficult to produce two identical sections in order to provide a good comparison between the experiments,
- Compared to the synaptosomes, the microcube samples are more stable and have a longer service life because they preserved their physiological environment,
- Compared to the studies on the living animal, the microcubes make it possible to carry out, from a single sacrifice, a series of tests that relate both to several compounds and to several levels of neurotransmission, which contrasts with the behavioral studies, where a tested animal makes it possible to answer only one question (active or not in a behavior whose scope is extrapolated).

The invention therefore also has as its object any preparation of microcubes of cerebral material as defined above. It preferably involves a composition that comprises at least 100 microcubes of cerebral material as described above. The invention also relates to the use of such microcubes or any other preparation that preserves the local connections for the identification of compounds that modulate the release of neuromediators.

As indicated above, an advantageous variant of the process of the invention consists in using a nerve tissue preparation that comprises foamy fibers of mammal cerebral material, in particular foamy fibers of the cerebellum or the hippocampus.

The foamy fibers contain glutamatergic nerve endings with a diameter of 5 to 10 µm. The latter are, in general, not preserved when the nerve tissue is homogenized for isolating small synaptosomes (0.5 µm). According to this invention, foamy fibers that are prepared so as to preserve said nerve endings are used as a nerve tissue preparation. These fibers can be prepared by fragmentation of the tissue in a gentler manner, in a physiological solution, which makes it possible to preserve these large glutamatergic endings. Foamy fibers that are prepared under these conditions and that can be used for the implementation of this invention are described in FIG. 2 in the attachment.

Other nerve tissue preparations can be used, such as cellular lines that express neurotransmission phenotypes, brain sections, cephalo-rachidian liquid, etc. In any case, it is particularly preferred, for the reasons mentioned above, to use preparations that preserve the local connections and that can be produced in a large number from a single animal, such as microcubes.

Bringing into contact the compound or compounds to be tested with the nerve tissue preparation can be carried out in any device that is suitable for a metering reaction, such as tubes, wells, plates, substrate, etc. It preferably involves tubes or microtitration wells. Typically, the meterings are carried out on titration plates.

The detection or the metering of one or more detectable substances if a neuromediator is released, or at least one product that results from the transformation of one of said substances if a neuromediator is released, can be carried out in various ways according to the nature of the substance to be metered.

In a particularly preferred implementation, the process uses cold substances, i.e., non-radioactive substances. The process relates very particularly to the detection or the metering of a substance that results in an emission of light in the presence of a neuromediator, whereby the metering of the substance then consists of the metering or the detection of the emitted light.

Thus, in a quite preferred method, the process of the invention comprises a metering by chemiluminescence, which makes possible fast, precise and numerous meterings of neuromediators. The substances or mixtures of products leading to an emission of light in the presence of the neuromediator can be, for example, according to the neuromediator, a combination of luminol and peroxidase, decaldehyde and luficerase or, for example, 1 a NADH-FMN oxidoreductase.

Thus, the process according to the invention is characterized in that at least one compound that is to be tested is brought into contact with a nerve tissue preparation in the presence of one or more enzymes whose substrate of at least one is a neuromediator and at least one agent that is able to emit the light following the degradation of said neuromediator by its enzyme.

As indicated above, the metering of the neuromediator can be carried out in the culture supernatant of the nerve tissue preparations after treatment of the latter to transform the neuromediator into a substrate of the light emission reaction. Thus, in a particular method, the metering consists in detecting a product for transformation of the neuromediator. For this purpose, the neuromediator is first treated to produce this transformation product. Different treatments can be used according to the neuromediator that is concerned.

By way of neuromediator whose release is detected or metered according to the process of the invention, it is possible to cite in particular glutamate (Glu), acetylquinoline (Ach), γ-aminobutyrate (GABA), the catecholamines, in particular dopamine (Da) or ATP.

The application of the process of the invention to the metering or the detection of the acetylcholine is characterized in that at least one compound that is to be tested is brought into contact with a nerve tissue preparation, then said preparation or its supernatant is brought into the presence, successively or simultaneously, of acetylcholinesterase, choline oxidase, peroxidase and luminol, and in that the light that is emitted by the degradation of the luminol following the degradation by acetylcholinesterase of the acetylcholine that is released by the nerve tissue preparation is detected or metered.

FIG. 3a that is in the attachment shows the metering of acetylcholine (Ach). For this metering, the mediator is hydrolyzed by the acetylcholinesterase, and the choline that results therefrom is oxidized by the choline oxidase in the presence of luminol and peroxidase. Even when a sample contains choline and ACh, it is possible to read the two substances sequentially: when the luminescence due to the choline is quenched, acetylcholinesterase is added, and the light that appears gives the Ach level. This type of test has been applied to some nerve samples that are basically non-mammalian or that do not permit studies on quite wide ranges of compounds (Israel and Morel, Rev. Neurol. 143 (1987) 89). This invention now shows that this type of test can be used on a large scale, on particular nerve tissue preparations and in a battery of tests with other neuromediator metering tests.

The application of the process of the invention to the metering or to the detection of glutamate is characterized in that at least one compound that is to be tested is brought into contact with a nerve tissue preparation, then said preparation or its supernatant is brought into the presence, successively or simultaneously, of glutamate dehydrogenase, oxidoreductase, luciferase, NAD and decaldehyde, and in that the light that is emitted by the degradation of the decaldehyde following the degradation by the glutamate dehydrogenase of glutamate released by the nerve tissue preparation is detected or metered.

FIG. 3b in the attachment shows the metering of glutamate. For this metering, the glutamate is dehydrogenated, for example, by the enzyme glutamate dehydrogenase; whereby the $NADH_2$ that appears is then attacked by the enzyme NADH-FMN oxidoreductase, which triggers a light emission in the presence of decaldehyde and photobacterium luciferase. This type of metering has been implemented under other conditions, experimental conditions, on the nerve endings of electric organs (Israel et al., Neurochem. Int. 22 (1993) 53). This invention now shows that this type of test can be used on a large scale, on particular nerve tissue preparations and in a battery of tests with other neuromediator metering tests.

The application of the process of the invention to the metering or to the detection of GABA is characterized in that at least one compound that is to be tested is brought into contact with a nerve tissue preparation, then said preparation or its supernatant is brought into the presence, successively or simultaneously, of gabase, oxidoreductase, luciferase, NAD and FMN and in that the light that is emitted by the degradation of SSAL following the degradation by the GABA gabase that was released by the nerve tissue preparation is detected or metered.

FIG. 3c in the attachment shows the metering of GABA. For this metering, the gabase enzyme is used to convert GABA into semi-succinic aldehyde with production of $NADH_2$. The semi-succinic aldehyde and the NADH trigger the emission of light in the presence of NADH-FMN oxidoreductase. The advantage of this test is that it is not necessary to add an exogenic aldehyde. This type of metering has been implemented under other conditions, experimental conditions, in nerve endings of electric organs (Israel and Lesbats. J. Neurochem. 67 (1996) 2624). This invention now shows that this type of test can be used on a large scale, on particular nerve tissue preparations and in a battery of tests with other neuromediator metering tests.

The application of the process of the invention to the metering or to the detection of catecholamines is characterized in that at least one compound that is to be tested is brought into contact with a nerve tissue preparation, then said preparation or its supernatant is brought into the presence, successively or simultaneously, of lactoperoxidase, $O_2$ and luminol and in that the light that is emitted by the degradation of the luminol following the degradation by the lactoperoxidase of a catecholamine that is released by the nerve tissue preparation is detected or metered.

FIGS. 3d and 3e in the attachment show the metering of catecholamines, in particular of dopamine. For the metering of the dopamine, this invention relates to a particularly effective test, based on the demonstration of the properties of an enzyme in the transformation of the dopamine. Thus, this invention shows that the enzyme lactoperoxidase, in the presence of $O_2$, results in the formation of $H_2O_2$, then, in the presence of the latter and luminol, the same lactoperoxidase catalyzes the light formation. Unexpectedly, the lactoperoxidase thereby appears to have both a conventionally described peroxidase action and an oxidase action.

This invention therefore also relates to a test that is based on a luminescent catecholamine and its applications to control the release of an adrenergic transmitter. An increasing number of oxidases have been used to measure their specific substrate (glucose, xanthine, choline, etc. (Michelson 1978 and Takayama et al. 1977). In the case of the acetylcholine transmitter (Ach), a process was proposed in 1980 in which the choline that results from the hydrolysis of the ACh was oxidized by the choline oxidase by forming hydrogen peroxide, whereby the latter is detected by using a chemiluminescent reaction (luminol plus peroxidase) (Israel and Lesbats, 1981 a, b, 1982, 1987). For other transmitters such as glutamate (Glu) or γ-aminobutyrate (GABA), the corresponding chemiluminescent test was found, and Glu and GABA are substrates for dehydrogenases that provide the NADH that triggers the luminescence of the bacterial luciferases that are sensitive to aldehydes (Fosse et al., 1986; Israel et al., 1993; Israel and Lebats, 1996). If ATP, detected by firefly luciferases (De Luca and McElroy, 1978; Meunier et al., 1975), is added to these transmitters, it is understood that many transmitters are now measured with chemiluminescent methods. In the case of the monoamines, the Tenne procedure for the monoamine oxidase converts the aliphatic amines into aliphatic aldehydes that trigger the luminescence of the bacterial systems that are sensitive to the long-chain aldehydes (Tenne et al., 1985 a, b).

The action of the monoamine oxidase on the catecholamines produces hydrogen peroxide (Cadet and Brannock, 1998) which could be detected with luminol. It has now been demonstrated within the framework of this invention that the milk lactoperoxidase has a mixed oxidase-peroxidase function; it has been capable of oxidizing catecholamines and catalyzing the reaction of the peroxide formed with the luminol, thus generating the emission of light. Thus, a sensitive test that measures norepinephrine, epinephrine or dopamine has been developed; it reacts very weakly with L-DOPA or serotonin. This test has been administered to control the release of catecholamines from tissues and adrenergic cells.

The invention therefore also has as its object a process for metering catecholamine in a sample, comprising bringing this sample into contact with the lactoperoxidase and the luminol, and the metering of the light that is emitted. The sample can be any nerve cell culture supernatant, brain microcubes or any other nerve tissue preparation, optionally after stimulation of the release of catecholamines by depolarization with calcium and incubation in the presence of the test compound. This metering can be used to meter epinephrine, norepinephrine, dopamine, etc.

The invention also relates to a kit for the implementation of a process that is described above. Such a kit comprises:

One or more preparations of nerve tissues in separate compartments,

One or more substances of which at least one can react with a neuromediator that is released by the nerve tissue preparation, and at least one of said substances can be detected if a neuromediator is released or of which at least one product that results from the transformation of one of said substances can be detected if a neuromediator is released, Optionally one or more reference compounds whose effect on the release of one or more neuromediators by the nerve tissue preparation is known.

Bringing the compound or compounds to be tested into contact with the nerve tissue preparation in a kit according to the invention can be carried out in any device that is suitable for a metering reaction, such as tubes, wells, plates, substrate, etc., It preferably involves tubes or microtitration wells. Typically, the meterings are carried out on titration plates.

Finally, the invention relates to the compounds that can modulate the pre-synaptic release of neuromediators that can be identified by a process according to the invention. More particularly, the invention relates to the use of such a compound for the production of a medication intended for treatment or prevention of diseases of the nervous system.

Actually, the compounds that are identified or characterized according to the process of the invention can either increase or inhibit the release of mediator. Thus, according to the pathologies involved, it may be advantageous to try to increase or to reduce the amount of released mediator. In this connection, the compounds that are identified can constitute compounds with therapeutic usage or else leads (targets) for the development of such therapeutic agents. The applications of these compounds are, for example:

For the compounds that modulate the release of acetylcholine, neurodegenerescence and Alzheimer's disease, For the compounds that modulate the release of glutamate, neurotoxicity and ischemia, For the compounds that modulate the release of GABA, epilepsy and anxiety, For the compounds that modulate the release of catecholamines (dopamine), psychosis, depression, Parkinson's disease, For the compounds that modulate the release of ATP, anxiety, panic, phobias, Parkinson's disease.

Other advantages and characteristics of the invention will emerge from the following examples, provided as illustrative and nonlimiting examples that describe the chemiluminescence meterings of four mediators (ACh, Glu, GABA and Da) on a preparation of microcubes of cerebral material and on foamy fibers. Other preparations, of course, that enter within the framework of this invention are also available, such as the cells that express various neurotransmission phenotypes, the measurement of glutamate from the cephalo-rachidian liquid to evaluate the excito-toxicity.

Reference will be made below to the accompanying drawings, in which.

Figure 3D:
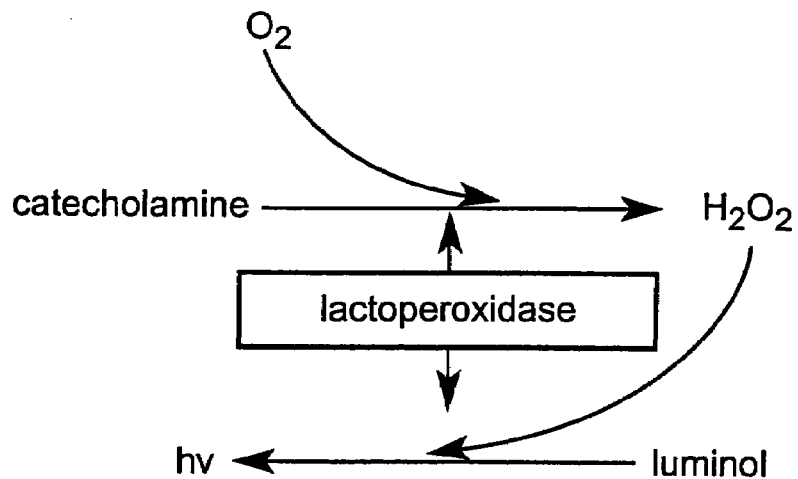
Figure 3E:
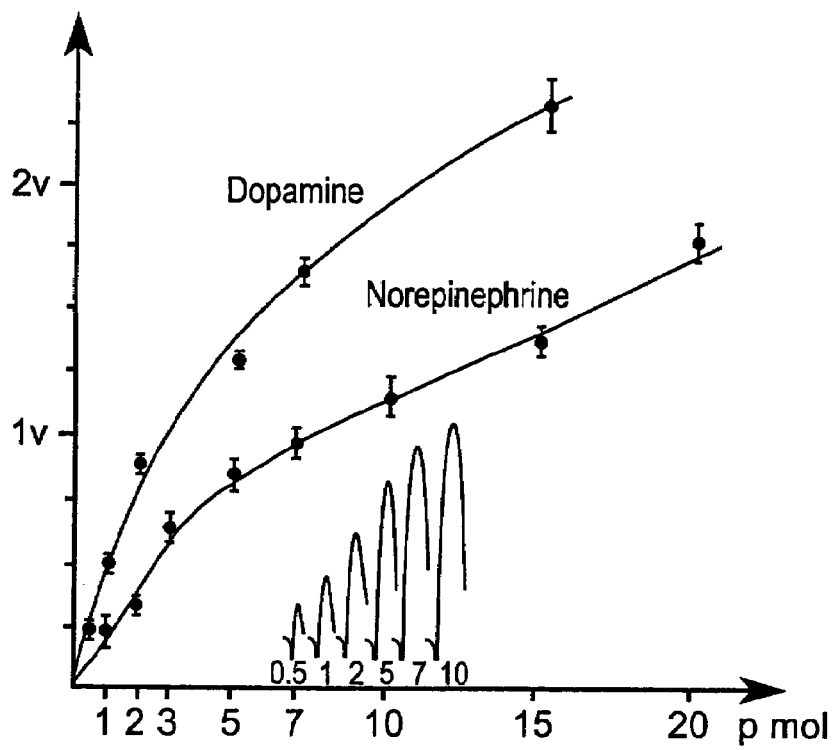

FIG. 3 shows the principle of meterings of acetylcholine (FIG. 3*a*), glutamate (FIG. 3*b*) and GABA (FIG. 3*c*). FIG. 3*d* shows the principle of the catecholamine-luminescent test, and FIG. 3*e* shows the metering of dopamine and norepinephrine. The various meterings make it possible to detect a few picomoles of one of the mediators. A relationship is shown between the emitted light and the mediator level in the figures for each mediator.

Figure 4:
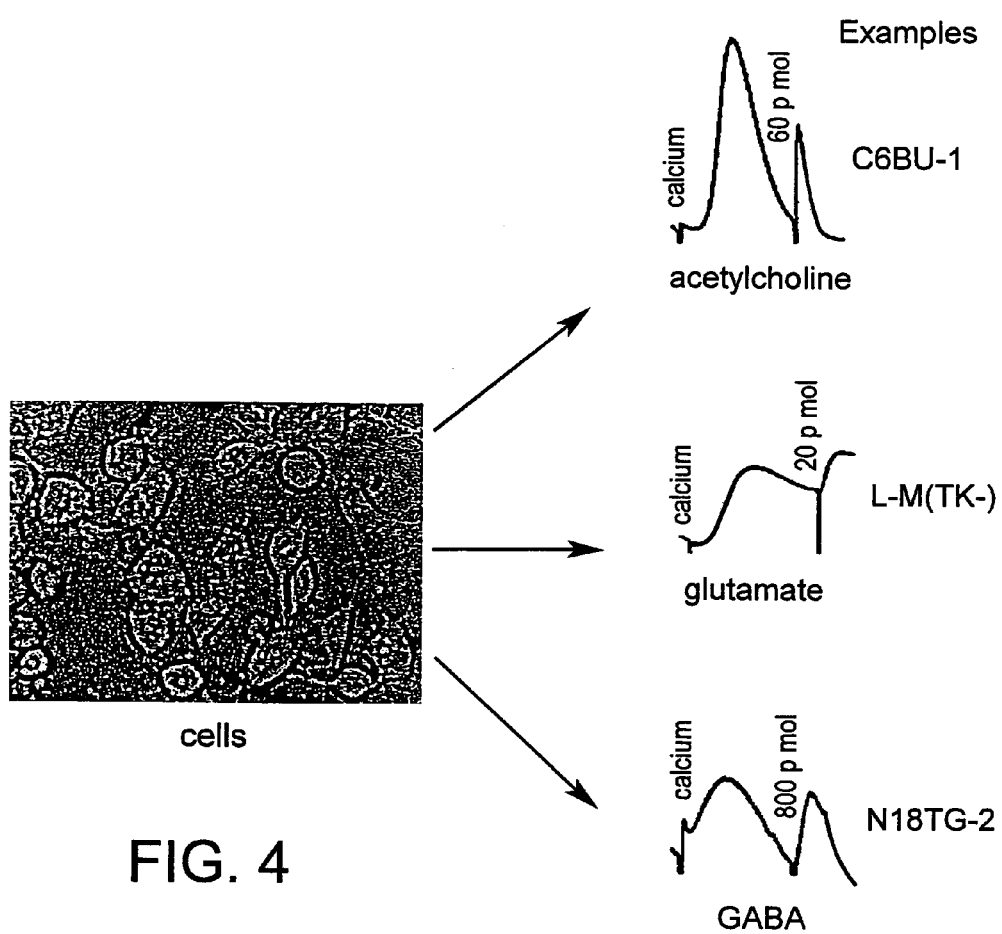

FIG. 4 shows the filling of cells by neuromediators and their use for the metering of neuromediators. The cells are charged with neuromediator by adding it to the culture center (10 mmol). The cells are washed 5 to 6 times, then recovered in a medium volume to end at a concentration of 1 nanomol of neuromediator in about 5 µl. Various neurotransmitter phenotypes are thus expressed by the cellular lines.

Figure 5:
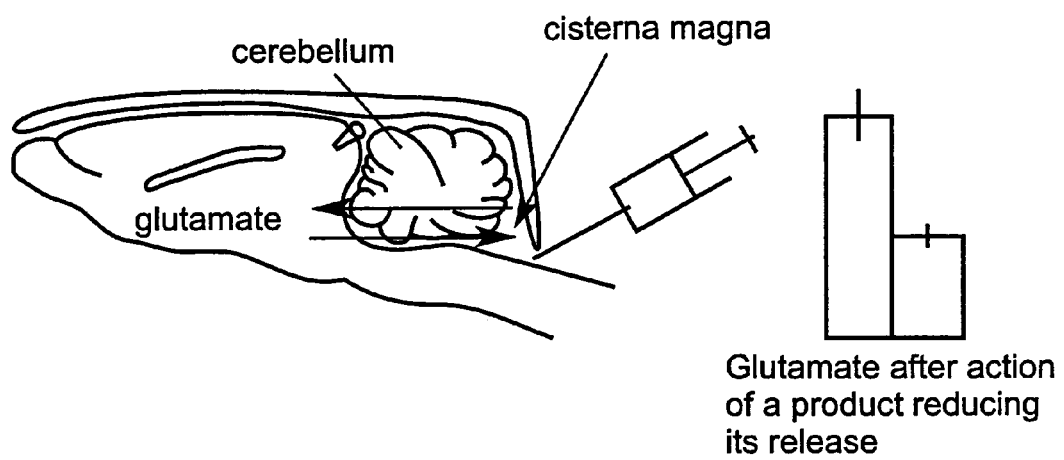

FIG. 5 shows the metering of the glutamate in the cephalo-rachidian liquid.

Figure 6A:
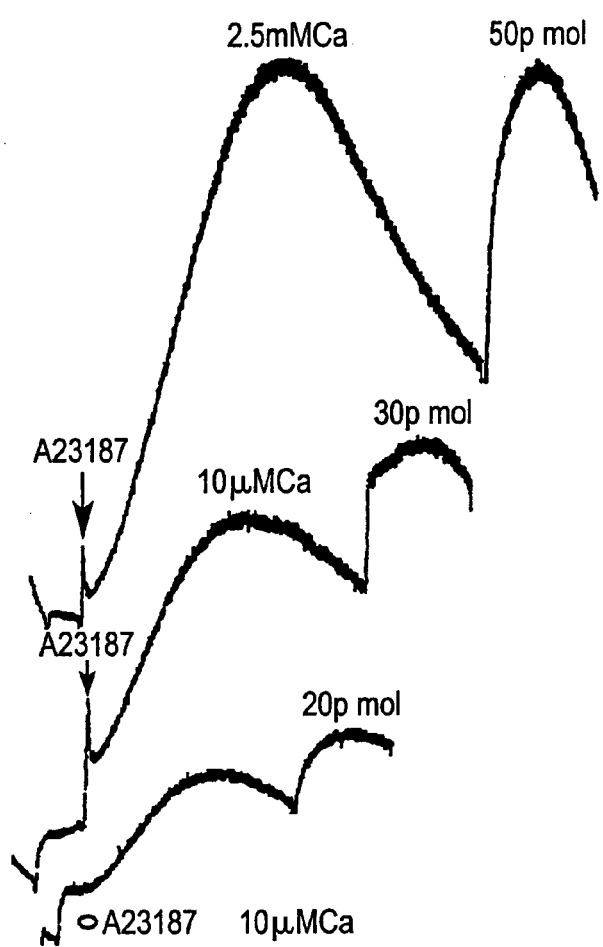
Figure 6B:
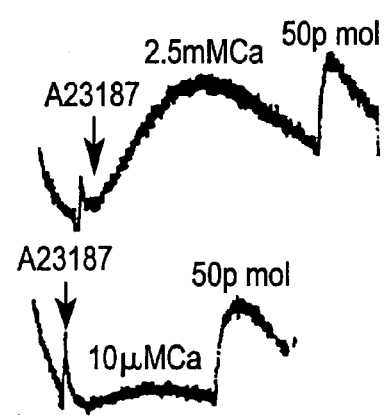

FIG. 6 shows the metering of catecholamines onto a preparation of dissociated adrenergic cells, in saline solution (A) or non-saline solution (B).

FIG. 7 shows the metering of catecholamines onto a brain microcube preparation that is stimulated by KCl in the presence of calcium (7A) or EGTA (7B).

Figure 8:
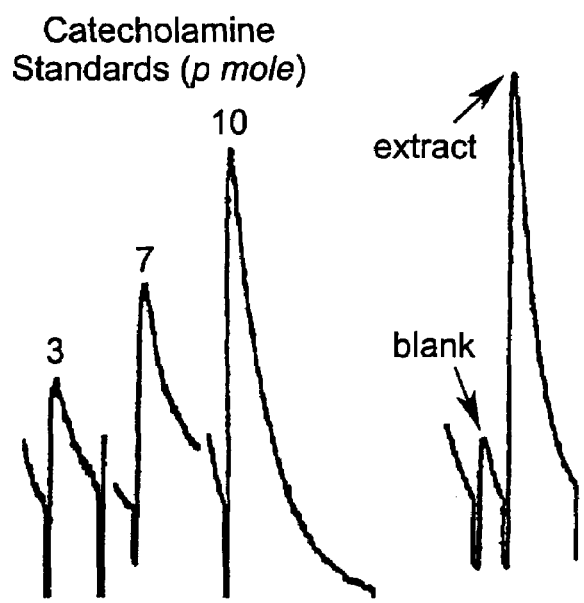

FIG. 8 shows the determination of the catecholamine content of the biological extracts.

Figure 9:
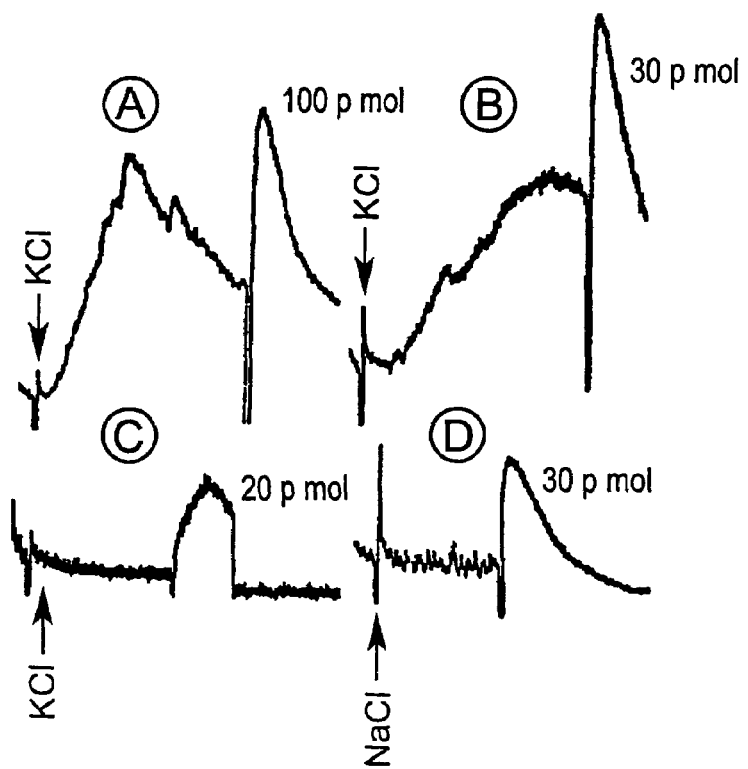

FIG. 9 shows the release of catecholamine by adrenal gland fragments.

FIG. 10 shows the release of catecholamines by the dopamine-enriched neuroblastoma cells during their cultivation.

EXAMPLE 1

Material and Methods

The lactoperoxidase (EC 1.11.1.7) of bovine milk was obtained from Sigma in freeze-dried powder form (80-150 units/mg of protein). The luminol (5-amino-1,2,3,4-tetrahydrophthalazine-dione-1,4) was obtained from Merck. A 1 mmol stock solution was prepared by diluting 18 mg in several drops of 1 M NaOH, and the final volume was brought to 100 mmol by adding 0.2 M tris buffer, pH 8.6.

The mammal Krebs medium consists of 136 mmol of NaCl, 5.6 mmol of KCl, 2.2 mmol of $CaCl_2$, 1.2 mmol of $MgCl_2$, 1.2 mmol of sodium phosphate, 2.5 mmol of sodium bicarbonate, and 5.5 mmol of glucose, oxidized.

EXAMPLE 2

Figure 1:
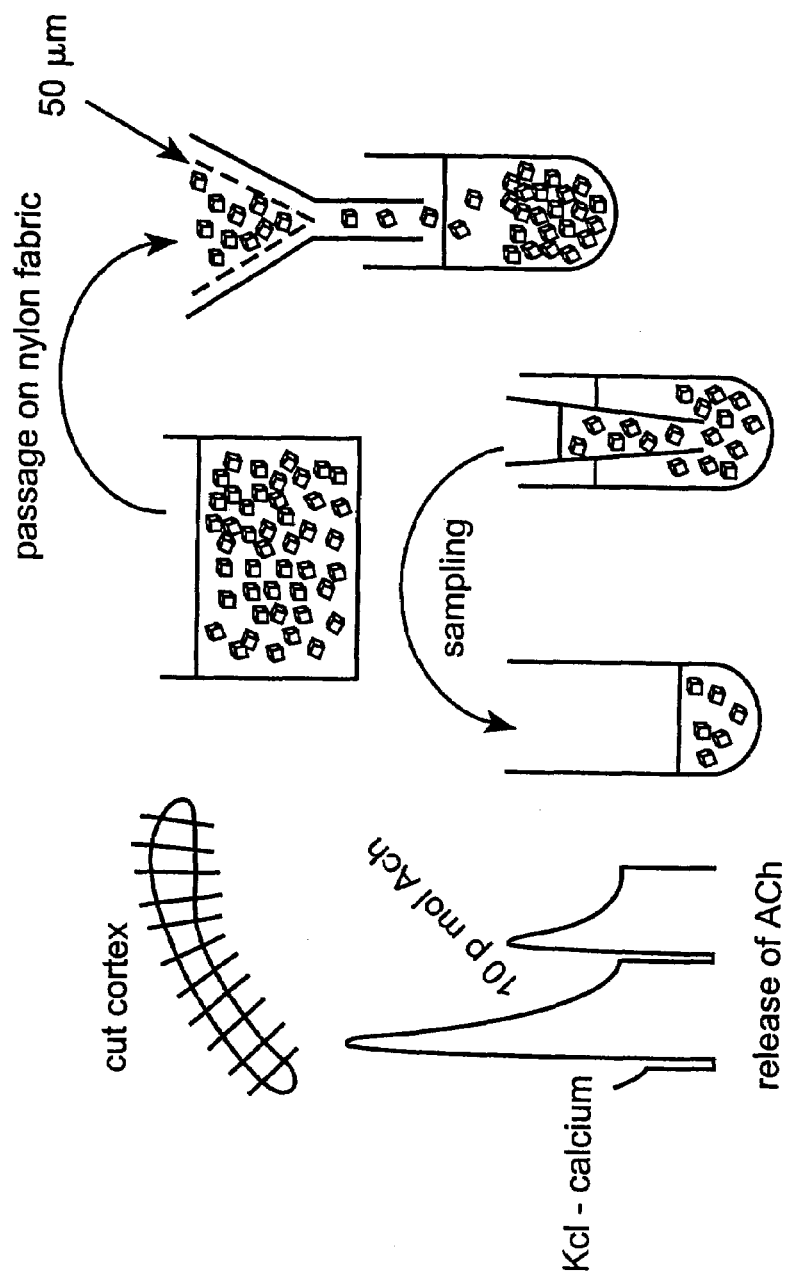
FIG. 1 shows the production of microcubes of cerebral material and their use for the metering of neuromediators.

Preparation of Microcubes of Cerebral Material and uses for the Metering of Neuromediators (FIG. 1)

The cortex of a rat or a mouse (or another mammal, including a human) is dissected and cut into cubes of about 1 to 2 $mm^3$ with a scalpel blade. These cubes are washed in a volume of mammal Krebs solution (at least twice 250 ml) then drawn in with a P5000 pipette and "jet"-forced through a rigid nylon fabric that has a mesh of about 1 mm on a side. The thus calibrated cubes are harvested at the bottom of a beaker by spontaneous sedimentation, which reduces the more "traumatizing" centrifugations, then the microcubes are harvested in a gradually smaller volume. The microcubes sediment out at the bottom of a conical tube and are covered with 1 or 2 ml of Krebs solution. When 20 to 50 µl of these microcubes are pipetted into a cap with a yellow-ended pointed Gilson pipette at the end that is cut to enlarge the inlet, an equal number of microcubes is sampled such that it is possible to test the release of mediator on statistically comparable samples. It is possible, for example, to incubate samples of 50 µl of microcubes with a series of compounds at various concentrations and to analyze their effects on the release that is spontaneous or induced by depolarization with potassium relative to a control. In contrast, the meterings of four neuromediators can be distributed over several days since these preparations can be frozen.

This method has been implemented particularly effectively in the case of ACh, GABA, glutamate or dopamine (FIG. 3). With regard to glutamate, a more suitable preparation is described that consists in the measure of the release of this mediator from nerve endings of foamy fibers of the cerebellum or the hippocampus.

EXAMPLE 3

Figure 2:
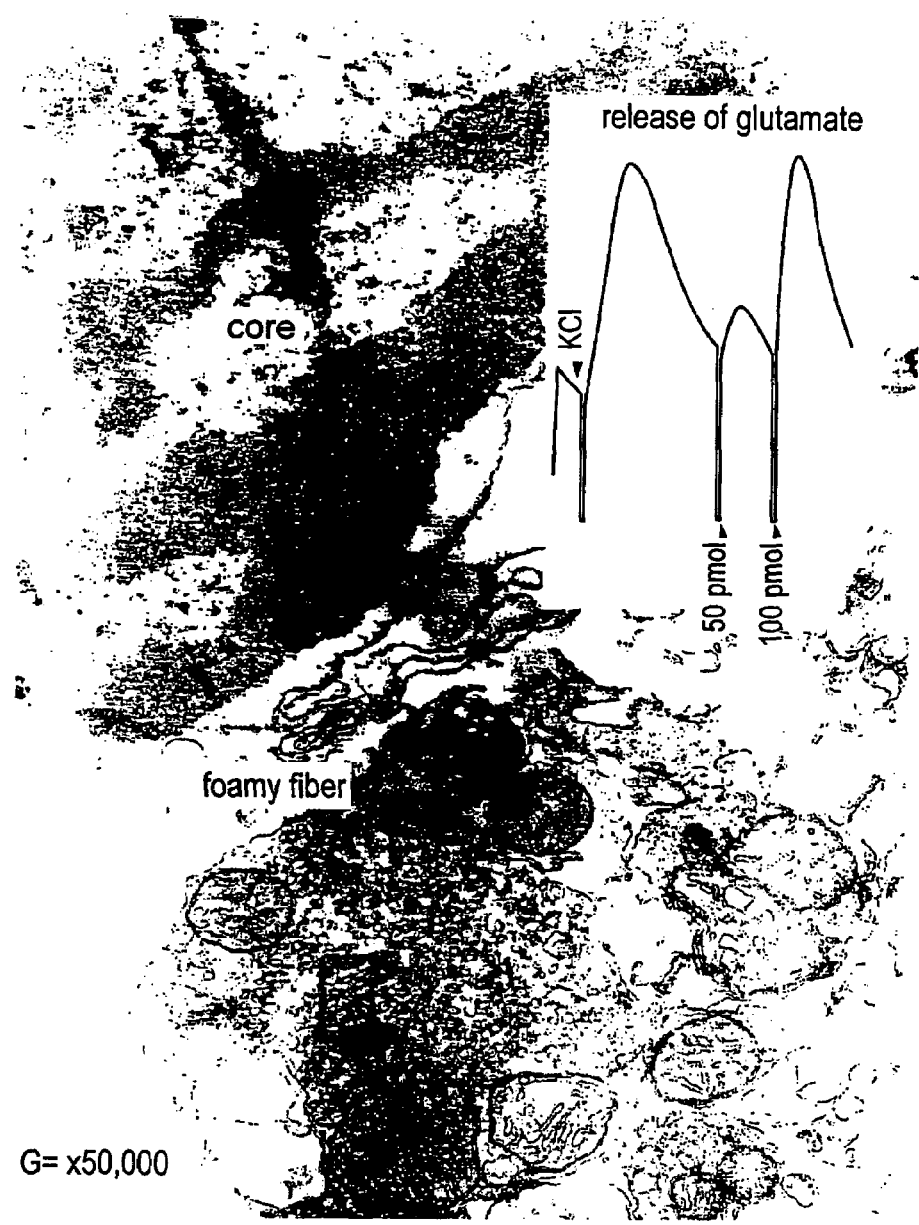
FIG. 2 shows the production and the appearance of glutamatergic foamy fibers and their use for the metering of neuromediators.

Preparation of Glutamatergic Foamy Fibers of the Cerebellum or the Hippocampus and uses for the Metering of Neuromediators (FIG. 2)

The nerve endings of foamy fibers have a diameter of 5 to 10 µm (FIG. 2) and are not, in general, preserved when the nerve tissue is homogenized to isolate small synaptosomes (0.5 µm) which are usually purified. If the precaution of fragmenting the tissue more gently into a physiological solution is taken, it is possible to preserve these large glutamatergic endings. To this end, amounts of tissue of about 0.1 g were dissociated by intake-expiration in a volume of 0.3 ml with a blue-ended pointed Gilson pipette. This "homogenate" is then brought back to 2 ml of Krebs solution and filtered on a 50 µm nylon fabric. The nerve endings of the foamy fibers spontaneously sediment out in the nuclear fraction. This cap is washed once or twice in Krebs solution by spontaneous sedimentation then resuspended in 1 ml of Krebs solution. These nerve endings will release the mediator when they are depolarized in the presence of calcium and will be stable for a long time.

To study the effect of compounds on the release of glutamate, in general 3 to 5 µl of this suspension, which is added to the reaction medium for metering glutamate, is used, whereby the release is triggered by the addition of KCl in the presence of calcium. The results that are obtained show that this nerve tissue preparation constitutes a material of choice for repeated metering, over a large number of samples.

EXAMPLE 4

Cellular Lines that Express Various Neurotransmission Phenotypes (FIG. 4)

It was shown that it was possible to load cells into cultures with one of three mediators ACh, Glu or GABA by adding it for 5 to 12 hours to the culture medium (Israel et al., Neuropharmacology 36 (1997) 1789). The technical methods are different for each mediator. In the case of ACh, for example (FIG. 4), it is necessary first to block the cholinesterases (50 µmol of phospholine). In all of the cases, however, the mediator intracellular concentration becomes close to the extracellular concentration that is used (here, mmol), but it is possible to bring it to 40 mmol. After the medium is washed, the cells guard the incorporated mediator. The comparison of the contents of ACh, GABA and Glu of various cellular lines is carried out by lyzing several µl of the suspension in the measuring medium, with 0.5% or 0.05% Triton for the cells that are charged with ACh or Glu respectively, and by bringing them first to 80° C. for the GABA then by metering the thus released mediator. Some cellular lines preferably release ACh, others the GABA or the glutamate (FIG. 4). Even if the microcubes constitute a material of choice, these lines can also be used in the processes of the invention for the identification or the characterization of compounds that are able to modulate the release of neuromediators.

EXAMPLE 5

Study of Excito-Toxicity of Glutamate Measured in the Cephalo-Rachidian Liquid (FIG. 5)

The alterations of the central nervous system due to a local lesion often touch on tissue territories that are more extended than those of the lesion per se. The area for diffusion of the exciter amino acids (glutamate) that are released around the site seems to correspond to this excito-toxic effect. To the extent that the extracellular space is balanced with the cephalo-rachidian liquid, it is possible to envisage that compounds that would reduce the glutamate content of the cephalo-rachidian liquid could limit the excito-toxicity and prevent the extension of alteration zones. The experiment that is carried out in FIG. 5 shows, by way of example, that a product that reduces the release of glutamate brought about a reduction in glutamate in the cephalo-rachidian liquid of the treated animals.

EXAMPLE 6

Study of the Release of Catecholamines

The invention relates very particularly to the development of a particularly effective test for metering, by chemiluminescence, catecholamines in nerve tissue preparations. This test is based on the unexpected double transformation of catecholamines by lactoperoxidase, leading to the emission of light, as it is shown in FIG. 3d. For the implementation of this test, the sample that comprises the neuromediator is brought into contact with the lactoperoxidase and the luminol. Equal volumes of these reagents are preferably first mixed (for example 30 µl of each), and the mixture is then added to the sample (about 6 µl). The reaction is preferably carried out in a saline solution that consists of 136 mmol of NaCl, 5.6 mmol of KCl, 1.2 mmol of $MgCl_2$, 20 mmol of tris buffer, pH 8.6, oxidized (solution I). The solution is placed in a tube and introduced into the luminometer, while being stirred gently. When the initial emission decreases to reach a base level, the mixture can be used to meter the catecholamines. For a metering under standard conditions, about 3 µl of each reagent is used (or 6 µl of the mixture). For a less sensitive metering, it is possible to use about 3 µl of luminol and 5 µl of lactoperoxidase in a non-saline solution that consists of 120 mmol of sucrose, 120 mmol of tris buffer, pH 8.6, oxidized (solution II).

The catecholamine metering was carried out from various nerve tissue preparations, including the dissociated adrenergic cells, the microcubes of striatal regions of the brain or cellular lines that are charged with catecholamine.

Dissociated adrenergic cells have been prepared and used in a dopamine release test. For this purpose, 4 adrenergic glands have been dissociated in a final volume of 2 ml of mammal Krebs medium. The release has been tested on volumes from 5 to 10 µl, in solutions I or II above in which the luminol (3 µl) and the lactoperoxidase (5 µl) have been added. The release of catecholamine was stimulated by the addition of calcium ionophore A23187 (1.2 µl) in the presence of calcium (2.5 mmol). The results that are obtained are presented in FIG. 6 and show that the test of the invention makes possible a quick and sensitive metering of the catecholamine release in small nerve tissue samples.

Microcubes from striatal regions of the brain have been prepared from the brains of two mice, which have been cut out and passed through a nylon membrane (0.5 mm in section), then recovered in a final volume of 2 ml in a conical tube. Samples of 10 µl of the cap were used to carry out the release test under the conditions that are described above (in 2 ml of solution I that contains 3 µl of luminol and 3 µl of lactoperoxidase). The release was stimulated by depolarization with KCl (45 mmol) in the presence of calcium (2.5 mmol). Controls without calcium were carried out in the presence of EGTA (7 µm). The results that are obtained are presented in FIG. 7 and show that the process of the invention is sensitive and makes it possible to meter the released neurotransmitter in response to the calcium. This test can be easily used for the identification or the characterization of compounds that actuate this release of dopamine.

Similar experiments have been carried out from cellular lines that are charged with dopamine (in particular neuroblast lines) and allowed the confirmation of the sensitivity and the reproducibility of the process of the invention.

EXAMPLE 7

Study of the Release of Catecholamines

This example that is more detailed than Example 5 describes a test that is based on a luminescent catecholamine and its applications for controlling the release of an adrenergic transmitter.

1) Material and Methods.

a) Solutions and Buffers.

Solution I: Consists of 136 mmol of NaCl, 5.6 mmol of KCl, 1.2 mmol of $MgCl_2$, and 20 mmol of tris buffer, pH 8.6, oxidized.

Solution II: Consists of 120 mmol of sucrose, and 120 mmol of tris buffer, pH 8.6, oxidized.

Mammal Krebs medium: 136 mmol of NaCl, 5.6 mmol of KCl, 2.2 mmol of $CaCl_2$, 1.2 mmol of $MgCl_2$, 1.2 mmol of Na phosphate, 2.5 mmol of Na bicarbonate, and 5.5 mm of glucose, pH 7.4, oxidized.

b) Stock Solutions.

The lactoperoxidase (E C 1.11.1.7) of cow's milk was bought from Sigma in the form of a freeze-dried powder (80 to 150 units per mg of protein); it was dissolved in 1 ml of water and kept frozen by 100 µl aliquots.

The luminol (5-amino-1,2,3,4-tetrahydrophthalazinedione-1,4) was bought from Merck. A stock solution was prepared by dissolving 18 mg of luminol in several drops of 1 M NaOH, and the volume was brought to 100 ml with 0.2 M tris buffer, pH 8.6.1 ml aliquots were kept at −20° C.

c) Reaction Mixture.

In 2 ml of solution I, the inventors added 3 µl of luminol and 311 of lactoperoxidase. It appeared preferable to mix an equal volume (30 µl of each) and to add 6 µl of the mixture that is kept in ice. The tube is placed in the luminometer and the solution mixed with a small magnet. When the initial flash has diminished into a baseline that slowly decreases, the mixture can be used to measure the catecholamines (norepinephrine, epinephrine, dopamine). If a less sensitive test is necessary, solution II is used, to which are added 3 μl of luminol and 5 μl of lactoperoxidase.

d) Tissue Extracts.

50 to 100 mg of tissues is cut and extracted for two hours in 1 ml of trichloroacetic acid (TCA) that is cooled in ice, and the denatured proteins are centrifuged and the supernatant is sampled. A 0.25 ml aliquot was diluted by half in the water and washed with ether four times to draw off the TCA (final pH: 4). The ether traces in the aqueous phase were evaporated. A sample is diluted 1/10 to 1/100 in solution I, and 0.5 ml is washed in 2 ml of chloroform. Then, 40 μl aliquots of the aqueous phase were treated with 10 μl of Triton X100 at 1%, and the determination was carried out on 3 to 5 μl. Each sample is compared to the standards, and it is essential to test a treated blank exactly as the sample. If the level of the blank is high, it is necessary to dilute the Triton until the blank becomes negligible by comparison with the sample (see FIG. 3).

e) Release of Catecholamines from Fragments of Adrenal Material.

Two mice were anesthetized with ether, then their adrenals were extracted and cut into 4 or 5 pieces that were washed for 1 hour and 40 minutes in 400 ml of mammal Krebs solution. The release was carried out in solution I or II in which the luminol and the lactoperoxidase are increased respectively up to 5 and 10 μl. The depolarization with 60 mmol of KCl in the presence of 2.5 mmol of calcium triggers the release.

f) Release of Catecholamines from Dissociated Adrenergic Cells.

The pieces were washed as above and dissociated by several intake and release cycles through a pipette (Eppendorf, 1 ml cone) in a final volume of 2 ml. The release was tested on 5 and 10 μl aliquots. Any more material quenches the reaction mixture. The release was measured in solution I or II in which the luminol (3 μl) and the lactoperoxidase (5 μl) were added. The release was triggered by the addition of calcium ionophore A23187 (1.2 μm) in the presence of 2.5 mmol of calcium.

g) Release of Catecholamines from Striatal Brain Microfragments.

The striatal regions of the brain of two mice were cut out and forced with large volumes of Krebs solution through a rigid nylon mesh (0.5 mm). The microfragments were collected at the bottom of the beaker and concentrated in a final volume of 2 ml in a conical tube. The cap is quickly formed by sedimentation, and it is possible to remove 10 μl samples from the cap. They are added in 2 ml of solution I that contains 6 μl of the lactoperoxidase-luminol mixture (an equal volume of each stock solution). The release was obtained by depolarization with KCl (45 mmol) in the presence of 2.5 mmol of calcium. The controls without calcium were carried out with 0.7 μm of EGTA in the solution. More EGTA could inhibit the reaction; this condition provides as much sensitivity for the controls as for the samples.

h) Release of Catecholamines from Dopamine-Enriched Cells.

Cell cultures NG108-15 were maintained in 2 mmol of glutamine-enriched Dulbecco's Modified Eagle Medium (DMEM), 10% fetal calf serum, HAT (100 μm of hypoxanthine, 1 mmol of aminopterin and 16 μm of thymidine). The cells were cultivated at 37° C. in a humidified atmosphere of 95% air and 5% $CO_2$. To charge the cells with dopamine, the inventors added, 16 hours before the experiment, a mixture of dopamine and neutralized ascorbic acid to obtain a final concentration of 10 mmol of each in the culture receptacle. The stock solution was made with 0.5 M ascorbic acid, neutralized by soda, and with 0.5 M dopamine, pH 8.7. The cells are washed in a solution that consists of 136 mmol of NaCl, 5.6 mmol of KCl, 1.2 mmol of $MgCl_2$, 20 mmol of tris buffer, pH 8.6, and 5.5 mmol of glucose, oxidized. Four washing cycles at 1200 rpm for 5 minutes were carried out. The cap that is obtained from 4 receptacles was resuspended in 0.5 ml of Krebs solution.

The release of enriched cells was carried out in 2 ml of solution II that contains 3 μl of luminol and 5 μl of lactoperoxidase; it was found to be preferable to reinforce the reaction mixture after having added the cells (5 μl) by doubling the luminol and the peroxidase and by adding 1 ml more of solution II. When the plot returned to an acceptable base level, the release was triggered by calcium (1.6 mmol) in the presence of ionophore A 23187 (0.7 μm).

i) Histochemical Localization of the Dopamine.

The cells were diluted by half with a solution at 2% of volume to the volume of glyoxylic acid containing 0.5 mg % of $MgCl_2$, pH 5. The cells were deposited on a glass strip, and the solution was drained. The cells were dried at ambient temperature and then treated at 80° C. for a half-hour before being examined in the medium that is suitable for observations of fluorescence. The procedure was adapted by Liu et al., 1992 following De La Torre 1980 and Knigge et al., 1977.

j) Figures.

FIG. 3d shows the principle of the catecholamine-luminescent test.

The lactoperoxidase catalyzes the oxidation of catecholamines (dopamine, norepinephrine, epinephrine) and the chemiluminescent oxidation of luminol; it has a mixed oxidase-peroxidase function.

FIG. 3e shows the dose-response curve for dopamine and norepinephrine.

The reaction mixture, solution I that contains lactoperoxidase and luminol (see Methods), provides a chemiluminescent reaction when the catecholamine is added. Below the curves is shown a typical response in the picomole range. The difference between the two curves depends on the lactoperoxidase lot and the solutions; it does not correspond to a specific distinction between the two catecholamines.

FIG. 6 shows the release of catecholamines by dissociated adrenergic cells.

In A, the release was measured in saline solution I; it was induced by the addition of ionophore A23107 (1.2 μm) in the presence of 2.5 mmol of calcium (top plot). When the calcium was reduced to 10 μm, the release is clearly weaker but significant (center plot). In the center plot, the spontaneous losses of the cells are measured in the absence of ionophore.

In B, the release was measured in solution II (sucrose-tris) and was brought about by the addition of ionophore as in A, in the presence of 2.5 mmol of calcium or 10 μm of calcium (bottom plot). In this solution, the release appears to be negligible in the presence of small amounts of calcium, and the spontaneous losses cannot be measured.

The proportion of lactoperoxidase and luminol is given in the Methods part.

FIG. 7 shows the release of catecholamine via striatal microfragments.

The striatum pieces were forced with large volumes of Krebs solution through a rigid nylon mesh; the microfragments were then able to sediment out and the striatum of 4 mice was concentrated in a volume of 2 ml. On the top plot, the release of catecholamine (probably dopamine) was brought about by KCl (45 mmol) and calcium (2.5 mmol). When the release diminishes, two dopamine standards were injected. On the bottom plot, a control depolarization was carried out as above, but in the absence of calcium (plus 0.7 µm of EGTA); no release was measured, and a standard was injected to verify the reaction mixture. In the two cases, 10 µl of the microfragments taken from the cap (see Methods) was used. The release was carried out in solution I that contains lactoperoxidase and luminol, as described in Methods.

FIG. 8 shows the determination of the catecholamine contents of the biological extracts.

The extract that washed with TCA and ether was also treated with chloroform and Triton, as described in Methods. The catecholamine content of the striatum extract is compared to standards (left) and to a blank that is treated exactly like the sample.

FIG. 9 shows the release of catecholamine via adrenal gland fragments.

Each mouse adrenal gland was cut into 4 pieces that were washed in a large volume (400 ml) of mammal Krebs solution. The pieces were transferred into solution I (A) or solution II (B) and the release brought about by the depolarization by the KCl (60 mmol) in the presence of calcium (2.5 mmol). The proportions of lactoperoxidase and luminol are given in the Methods part. The bottom plots are controls that are carried out in the absence of calcium (C) or in the absence of depolarization (D) by using 60 mmol of NaCl.

FIG. 10 shows the release of catecholamine by dopamine-enriched neuroblastoma cells during their cultivation.

Top: Histochemical demonstration of the presence of dopamine in culture-enriched NG108-15 cells with dopamine (2 mmol). The process with glyoxylic acid provides a fluorescent compound with the dopamine. The cells were enriched with 2 to 10 mmol of dopamine.

Bottom: Release of dopamine via the enriched cells. The NG108-15 cells were enriched with 10 mmol of dopamine added for 12 hours to the culture. Cells from four confluence receptacles were assembled, washed at least four times in a saline solution and suspended in 0.5 ml of saline solution.

Left: The release was measured on 5 µl of cellular suspension in solution II that contains lactoperoxidase and luminol as described in Methods. The release was brought about by calcium (1.6 mmol) and A23187 (0.7 µm). Two dopamine standards were injected to calibrate the release.

Right: Control, the dopamine-enriched cells were not released in the absence of calcium (the NaCl injection replaces the calcium). The standard shows that the reaction mixture would have detected any released dopamine.

2) Results a) Test of Luminescent Catecholamines.

The test that is described results from experimental observations that show that the dopamine or the norepinephrine trigger the chemiluminescent oxidation of luminol in the presence of lactoperoxidase. The simplest interpretation of the reaction is to consider that the lactoperoxidase has an oxidase activity forming, from catecholamines and molecular oxygen, hydrogen peroxide that reacts with luminol; lactoperoxidase catalyzes this chemiluminescent reaction as any peroxidase would do. FIG. 3d shows a diagram of the possible oxidase-peroxidase function of the lactoperoxidase. FIG. 3e illustrates two dose-response curves that are obtained with norepinephrine and dopamine. The difference between the two curves reflects only the properties of the enzyme preparation and mixture used in the two experiments. Below the curves are shown typical flashes of light that are obtained in the range of 0.5 to 10 picomoles for the dopamine. Equivalent responses have been recorded for norepinephrine or epinephrine. The test does not measure the L-DOPA that has a slow increase of the baseline. The L-DOPA deactivated the reaction mixture, which lost its sensitivity to the subsequent addition of norepinephrine or dopamine. The reaction does not detect serotonin.

The evaluation of the contents of catecholamines of unknown biological samples requires an extraction and the treatment of samples that decreases or minimizes the possible interferences with other compounds that can be present in the extract, particularly the lipids. The sample that is washed with TCA and ether was also mixed with chloroform, and a small amount of Triton was added to the aqueous phase, as described in Methods. FIG. 8 shows a typical evaluation in which the catecholamine content of the sample is compared to standards; a blank is also produced with the solution treated exactly like the biological extract. Table I below provides the results for five different experiments; the catecholamine content, found with the chemiluminescent test, is compared to values that are found in literature by using fluorometry or other methods.

TABLE I

|  | Chemiluminescent Method | Fluorometric Method |
| --- | --- | --- |
| Adrenal gland | 490 ± 94 | 1100* |
| Striatum | 40 ± 10 | 54 ± 8.2** |
| Vas deferens | 11.9 ± 0.8 | 7.9*** |

Chemiluminescence method: mean ± SEM of 5 different experiments (µg per g of fresh tissue).
*Udenfriend (1962)
**Cattabeni et al. (1972)
***Cooper et al. (1978)

b) Release of Catecholamines from the Tissues and Cells.

As described above for the chemiluminescent processes, the catecholamines test can be adapted to follow the release from sections of tissues or cells. This required several modifications based on each of the experimental situations. In the case of adrenal sections, for example, one of the difficulties came from the presence of large extracellular amounts that quench the reaction mixture. In the case of cellular suspensions, the cloudiness of the solution and the lipid material quench the chemiluminescence and reduce the sensitivity. The inventors have finally been able to adapt the procedure for each experiment.

c) Release of Catecholamines by Fragments of Adrenal Material

Each gland has been cut into 4 or 5 sections washed twice in a large volume of mammal Krebs solution (see Methods). One section was gently transferred into a reaction mixture, solution I or solution II neutralized to pH 8.6 and containing lactoperoxidase and luminol at higher concentrations, as described in Methods. The release was brought about by depolarization with KCl in the presence of calcium. FIG. 9 (A, B, C, D) shows that the release was obtained both in a saline solution (A) and in a sucrose-tris solution (B) and that it clearly depends on calcium. Controls produced in the absence of calcium or after having injected NaCl instead of KCl are shown at the bottom of FIG. 9 (C and D).

d) Release of Catecholamines by Striatal Microfragments

The procedure was also tested on striatal sections, taken from mouse brains. In this case also, the fragments were washed in a large volume of Krebs solution and allowed to sediment out before being collected in 2 ml of Krebs solution. A material aliquot is taken from the cap and injected into the reaction mixture. In this case, the proportions of luminol and lactoperoxidase that are used in the test (see Methods) that provide maximum sensitivity have been kept. The release was also brought about by depolarization with KCl (FIG. 7, top plot), a control in the absence of calcium did not show the release of dopamine (FIG. 7, bottom plot). In the two cases, a standard with the dopamine showed that the reaction mixture was sensitive to the dopamine and that it allows an evaluation of the Ca release depending on the transmitter.

e) Release of Catecholamines from Cellular Suspensions

After having incubated the adrenal pieces in Krebs solution then having washed them to remove interfering substances, the pieces were dissociated by several intake cycles with the pipette; the suspension obtained from 4 adrenal glands was collected in a volume of 2 ml of Krebs solution. The release was carried out by using 5 to 10 µl of solution, and the use of more cells quenches the reaction mixture. FIGS. 6 A and B have as their object to compare the release of adrenal cells in two different solutions, saline solution I and non-saline solution II. In A, the release from cells was measured in saline solution and brought about by calcium ionophore (A23187) in the presence of 2.5 mmol of calcium. When the calcium is reduced to 10 µm, the release diminishes but it is not negligible (center plot). The lowest plot shows the spontaneous loss in the absence of ionophore or calcium.

FIG. 6 B shows that in a non-saline medium (solution II: sucrose tris), the release of these cells can also be brought about as in A by ionophore A23187 and calcium, but the dependency with calcium is more obvious since the release has become negligible in conditions of a low calcium level. In addition, the spontaneous losses were not detected in sucrose-tris. It is probable that a release behavior that does not depend on calcium, due to the swelling of the cells, takes place in saline solution.

f) Release of Dopamine from Cells in a Dopamine-Enriched Culture

Prior works showed that the cells in culture could be enriched with ACh, Glu or GABA by adding the transmitter in the culture medium (Israel et al., 1994, 1997). In the particular case of NG108-15 cells, the inventors found articles showing that they could incorporate serotonin or catecholamines (Furuya et al., 1985, Liu et al., 1992). They show here that the NG108-15 cells accumulate the dopamine of the culture medium to which 2 to 10 mmol of dopamine have been added. The catecholamines should be protected from auto-oxidation by using ascorbic acid, in particular for long incubation periods (see Methods). FIG. 10 (top) shows that the cells are actually enriched with dopamine. The histochemical characterization of the dopamine with the procedure with glyoxylic acid makes the cells fluorescent. The charged cells were able to release the neurotransmitter in response to the influx of calcium brought about by A23187 in the presence of calcium. In this case, it was necessary to reinforce the reaction mixture after having added the cells into solution II that contains reagents and ionophore. The extracellular dopamine is first measured and when the baseline is reached, an additional amount of luminol, lactoperoxidase and 1 ml of solution II (see Methods) was added. When the baseline was reached, the release was brought about with calcium ((FIG. 10, left plot). A control in which an injection of NaCl is carried out instead of calcium is shown in FIG. 10 (right plot). A release of clearly calcium-dependent dopamine was obtained from the charged cells.

3) Discussion.

When this project began, the inventors wished to couple the oxidation of catecholamines by monoamine oxidase to the detection of hydrogen peroxide by means of luminol. It was accidentally found that the lactoperoxidase was in itself sufficient to catalyze both the oxidation of the catecholamines and the detection of the product with the chemiluminescence of luminol. It is known that the catecholamines are detected by amperometric procedures and that these methods are sensitive; the specificity depends on the relationship between the oxidoreduction potential of the catecholamines and the detection electrode (Albillos et al., 1977, Pan et al., 1977). In this test, it is probable that the oxidoreduction takes place via the iron of the lactoperoxidase; it could be used as an electron donor in the "oxidase" stage and an electron acceptor in the action of the peroxidase on luminol. In all cases, the affinity of FeCl3 for the catecholamines is at the root of the "Vulpian reaction" which made it possible to discover adrenaline in the adrenergic circulation. It is then probable that the metallic ion of the peroxidase is essential for explaining the mechanism of the observed reactions.

The inventors also observed that the procedure does not distinguish the norepinephrine, epinephrine or dopamine and that L-DOPA cannot be measured despite the fact that it deactivates the reaction mixture. Other transmitters, such as the serotonin that is oxidized by the monoamine oxidase, have not reacted during the test with the lactoperoxidase. Other compounds, ascorbate or acetylcholine, have little or no effect.

The described process can be used in addition to other methods. The process is fast and completes the other methods developed for ATP, ACh, glutamate and GABA by using the same luminometer for determining the light emission.

The inventors were also able to control the release of catecholamines from various adrenergic preparations. The process makes it possible to detect the release continuously. One of the results that may be advantageous in the future is the observation that some cells can be enriched with dopamine during the cultivation. This could make it possible to find cells that can accumulate and release this transmitter, with the object of correcting, one day, a dopaminergic deficiency such as Parkinson's Disease (Bjorklund and Stenevi, 1985; Espejo et al., 1998). In addition, the method could be useful for finding pharmacological compounds that affect the adrenergic transmission.

BIBLIOGRAPHIC REFERENCES

Albillos, A.; Dernick, G.; Horstmann, H.; Almers, W.; Alvarez de Toledo, G.; Lindau, M. The Exocytotic Event in Chromaffin Cells Revealed by Patch Amperometry. Nature 1997; 389: 509-512.

Bjorkland, A.; Steveni, U. Intracerebral Neuronal Grafting. In: Neural Grafting in the Mammalian CNS, A. Bjorklund and U. Steveni, Eds., Amsterdam Elsevier. 1985; 3-14.

Cadet, J.; Brannock, C. Free Radicals and the Pathobiology of Brain Dopamine Systems. Neurochem Int 1998, 32: 117-131.

Cattabeni, F.; Koslow, S. H.; Costa, E. Studies of Neurotransmitters at the Synaptic Level. Edited by Costa, E.; Iversen, L. L.; and Paoletti, R. In: Advances in Biochemical Psychopharmacology. Raven Press NY. 1972; 6:51.

Cooper, J. R.; Bloom, F. E.; Roth, R. H. In: Biochemical Basis of Neuropharmacology (Third Edition). Oxford University Press 1978; 117.

De Luca, M.; McElroy, W. D. Purification and Properties of Firefly Luciferase. In Methods in Enzymology Bioluminescence and Chemiluminescence. Ed. M. A. De Luca Acad Press NY. 1978; LVII: 3-15.

De La Torre, J. C. An Improved Approach to Histofluorescence Using the SPG Method for Tissue Monoamines. J Neurosci Method 1980; 3: 1-5.

Espejo, E. F.; Montoro, R. J.; Armengol, A. J.; Lopez-Barneo, J. Cellular and Functional Recovery of Parkinsonian Rats After Transplantation of Carotid Body Cell Aggregates. Neuron 1998; 20: 197-206.

Fosse, M. V.; Kolstad, J.; Fonnum, F. A Bioluminescence Method for the Measurement of L-Glutamate; Application to the Study of Changes in the Release of L-Glutamate from Lateral Geniculate Nucleus and Superior Colliculus after Visual Cortex Ablation in Rats. Journal of Neurochemistry. 1986; 47; 340-349.

Furuya, S.; Sawada, M.; Nagatsu, T.; Suzuki, O.; Higashida, H. Localization of [³H]Serotonin in Neuroblastoma x Glioma Hybrid Cells. Brain Research 1985; 361: 77-90.

Israël, M.; Lesbats, B. Continuous Determination by a Chemiluminescent Method of Acetylcholine Release and Compartmentation in Torpedo Electric Organ Synaptosomes. Journal of Neurochemistry 1981 a; 37: 1475-1483.

Israël, M.; Lesbats, B. Chemiluminescent Determination of Acetylcholine and Continuous Detection of its Release from Torpedo Electric Organ Synapses and Synaptosomes. Neurochem Int. 1981 b; 3: 81-90.

Israël, M.; Lesbats, B. Application to Mammalian Tissues of the Chemiluminescent Method for Detecting Acetylcholine. Journal of Neurochemistry. 1982; 39: 248-250.

Israël, M.; Lesbats, B. The Use of Bioluminescence Techniques in Neurobiology, with Emphasis on the Cholinergic System. In: Neurochemistry, A Practical Approach (Turner, A. J.; Bachelard, H. S., Eds) IRL Press, Oxford 1987; 113-135.

Israël, M.; Lesbats, B. A Bioluminescent Aminobutyrate Assay for Monitoring its Release from Inhibitory Nerve Endings. Journal of Neurochemistry 1996; 67: 2624-2627.

Israël, M.; Lesbats, B.; Bruner, J. Glutamate and Acetylcholine Release from Cholinergic Nerve Terminals, A Calcium Control of the Specificity of the Release Mechanism. Neurochem Int 1993; 22: 53-58.

Israël, M.; Lesbats, B.; Synguelakis, M.; Joliot, A. Acetylcholine Accumulation and Release by Hybrid NG108-15, Glioma and Neuroblastoma Cells—Role of a 15 kDa Membrane Protein in Release. Neurochem Int 1994, 25; 103-109.

Israël, M.; Lesbats, B.; Tomasi, M.; Couraud, P. O.; Vignais, L.; Quinonero, J.; Tchelingerian, J. L. Calcium-Dependent Release Specificities of Various Cell Lines Loaded with Different Transmitters. Neuropharmacology 1997; 36: 1789-1793.

Knigge, K. M.; Hoffman, G.; Scott, D. E.; Sladek, J. R. Identification of Catecholamine and Luteinizing Hormone-Releasing Hormone (LHRH) Containing Neurons in Primary Cultures of Dispersed Cells of the Basal Hypothalamus. Brain Res 1977; 120: 393-405.

Liu, Y.; Peter, D.; Roghani, A.; Schuldiner, S.; Prive, G. G.; Eisenberg, D.; Brecha, N.; Edwards, R. H. A cDNA that Suppresses MMP+Toxicity Encodes a Vesicular Amine Transporter. Cell 1992; 70: 539-551.

Michelson, A. M. Purification and Properties of Pholas Dactylus Luciferine and Luciferase. In Methods in Enzymology Bioluminescence and Chemiluminescence. Ed. M. A. De Luca; Acad Press NY 1978; LVII; 385-406.

Mennier, F. M.; Israel, M.; Lesbats, B. Release of ATP from Stimulated Nerve Electroplaque Junction. Nature 1975; 257: 407-408.

Pan, C. Y.; Kao, L. S. Catecholamine Secretion from Bovine Adrenal Chromaffin Cells: The Role of $Na^+/Ca^{2+}$ Exchange and the Intracellular $Ca^{2+}$ Pool. J. Neurochem 1997; 69: 1085-1092.

Takayama, M.; Itoh, S.; Nagasaki, T. and Tanimizu, I. A New Enzymatic Method for Determination of Serum Choline-Containing Phospholipids. Clinica Chimica Acta 1977; 79: 93-98.

Tenne, M.; Finberg, J. P.; Youdim, M. B.; Ulitzur, S. A New Rapid and Sensitive Bioluminescence Assay for Monoamine Oxidase Activity. J. Neurochem 1985; 44: 1378-1384.

Tenne, M.; Youdim, M. B.; Ulitzur, S.; Finberg, J. P. Deamination of Aliphatic Amines by Monoamine Oxidase A and B Studies Using a Bioluminescence Technique. J Neurochem 1985; 44: 1373-1377.

Udenfriend, S. In Fluorescence Assay in Biology and Medicine. Acad. Press NY 1962; 1:158.

The invention claimed is:

1. A method of preparing calibrated pieces of mammalian cerebral tissue, the method comprising:
   (i) obtaining one or more samples of mammalian cerebral nerve tissue,
   (ii) cutting the one or more samples into pieces,
   (iii) washing the pieces in mammal Krebs solution,
   (iv) passing the pieces through at least one grid having a mesh size to produce calibrated pieces of mammalian cerebral tissue having a mean size between 0.1 $mm^3$ and 5 $mm^3$,
   (v) harvesting the calibrated pieces of mammalian cerebral tissue produced in step (iv) so that the final preparation comprises calibrated pieces of mammalian cerebral tissue having a mean size between 0.1 $mm^3$ and 5 $mm^3$ wherein at least some connections between neurons are maintained.

2. The method of claim 1, wherein said cerebral nerve tissue comprises an entire brain.

3. The method of claim 1, wherein said cerebral nerve tissue is selected from the group consisting of the cortex and the cerebellum of a brain.

4. The method of claim 1, wherein said mammal is selected from the group consisting of rat, mouse and human.

5. The method of claim 1, wherein said grid is a nylon or metallic grid.

6. The method of claim 1, wherein said mesh size is between 0.5 mm and 2 mm.

7. The method of claim 1, wherein said mesh size is between about 1 mm and 2 mm.

8. The method of claim 1, wherein cutting the one or more samples into pieces comprises cutting the one or more samples into pieces of about 1 to 2 $mm^3$.

9. The method of claim 1, wherein harvesting the calibrated pieces of mammalian cerebral tissue comprises collecting the calibrated pieces of mammalian cerebral tissue from the bottom of a receptacle after spontaneous sedimentation.

10. A composition of calibrated pieces of mammalian cerebral tissue obtained by the method of claim 1.

11. The composition of claim 10 comprising calibrated pieces of mammalian cerebral tissue in mammal Krebs solution.

* * * * *